US012773479B2

(12) United States Patent
Parthasarathy et al.

(10) Patent No.: US 12,773,479 B2
(45) **Date of Patent: *Oct. 27, 2026**

(54) PARYLENE COATINGS FOR MEDICAL ARTICLES THAT ARE CLEANABLE AND REDUCE MICROBIAL TOUCH TRANSFER

(71) Applicant: Solventum Intellectual Properties Company, Maplewood, MN (US)

(72) Inventors: Ranjani V. Parthasarathy, Woodbury, MN (US); Jodi L. Connell, St. Paul, MN (US); Audrey A. Sherman, Woodbury, MN (US); Daniel J. Rogers, Grant, MN (US)

(73) Assignee: Solventum Intellectual Properties Company, Eagan, MN (US)

( * ) Notice: Subject to any disclaimer, the term of this patent is extended or adjusted under 35 U.S.C. 154(b) by 245 days.

This patent is subject to a terminal disclaimer.

(21) Appl. No.: 18/681,925

(22) PCT Filed: Aug. 25, 2022

(86) PCT No.: PCT/IB2022/057985

§ 371 (c)(1),
(2) Date: Feb. 7, 2024

(87) PCT Pub. No.: WO2023/037197

PCT Pub. Date: Mar. 16, 2023

(65) Prior Publication Data

US 2025/0058026 A1 Feb. 20, 2025

Related U.S. Application Data

(60) Provisional application No. 63/241,132, filed on Sep. 7, 2021.

(51) Int. Cl.
*A61L 29/04* (2006.01)
*A61B 7/02* (2006.01)
*A61L 29/08* (2006.01)

(52) U.S. Cl.
CPC .......... *A61L 29/041* (2013.01); *A61L 29/085* (2013.01); *A61B 7/02* (2013.01); *A61L 2420/02* (2013.01)

(58) Field of Classification Search
None
See application file for complete search history.

(56) References Cited

U.S. PATENT DOCUMENTS 5,067,491 A 11/1991 Taylor, II
2008/0093157 A1 * 4/2008 Drummond .............. A61B 7/02 181/131

(Continued)

FOREIGN PATENT DOCUMENTS

CN 103132045 A 6/2013
EP 1830712 A1 9/2007

(Continued)

OTHER PUBLICATIONS

Optical Clarity of Parylene at Increased Thickness, 2023, Specialty Coating Systems, pp. 4-6 (Year: 2023).*

(Continued)

*Primary Examiner* — Thomas J Kessler

(57) ABSTRACT

Flexible medical articles have a barrier polymer coating that provides a cleanable surface and reduced microbial touch transfer. The articles may be flat or tubular. The articles are formed from a polymer composition containing one or more extractable components. The barrier polymer coating is a transparent vapor-deposited coating of a barrier polymer derived from at least one ethylenically unsaturated monomer. The vapor-deposited polymer coating barrier reduces the extraction of extractable component(s) from the tube.

(Continued)

The coating also provides a reduction in microorganism touch transfer of at least 20% and provides increased wet out of a cleaning solvent compared to an identical tube without the transparent vapor-deposited coating.

20 Claims, 3 Drawing Sheets

(56) References Cited

U.S. PATENT DOCUMENTS

| | | | | |
|---|---|---|---|---|
| 2008/0171087 | A1 | 7/2008 | Chappa | |
| 2010/0266794 | A1* | 10/2010 | Wright | C08F 290/061<br>264/496 |
| 2013/0045146 | A1* | 2/2013 | Peters | B01L 3/5635<br>422/547 |
| 2015/0165097 | A1* | 6/2015 | Parthasarathy | A61L 31/16<br>514/340 |

FOREIGN PATENT DOCUMENTS

| | | | |
|---|---|---|---|
| KR | 20030034119 | A | 5/2003 |
| WO | 9959646 | W | 11/1999 |
| WO | 200622854 | W | 3/2006 |
| WO | 200822258 | W | 2/2008 |
| WO | 200839749 | W | 4/2008 |
| WO | 2012166291 | A2 | 12/2012 |
| WO | 2020209828 | A1 | 10/2020 |
| WO | 2021032368 | A1 | 2/2021 |
| WO | 2021033151 | A1 | 2/2021 |
| WO | 2021033162 | A1 | 2/2021 |
| WO | 2021240254 | A1 | 12/2021 |
| WO | 2022123440 | A1 | 6/2022 |

OTHER PUBLICATIONS

Franklin Trevor et al, “Vapor-Deposited Biointerfaces and Bacteria: An Evolving Conversation”, Dec. 16, 2019 (Dec. 16, 2019), vol. {0} 6, No. {0} 1, p. 182-197.

Imani, “Flexible Hierarchical Wraps Repel Drug-Resistant Gram-Negative and Positive Bacteria”, ACS Nano, 2020, vol. 14, No. 01, pp. 454-465.

International Search Report for PCT/IB2022/057985, mailed on Nov. 29, 2022, 5 pages.

Mann, “Surface Micropattern Resists Bacterial Contamination Transferred by Healthcare Practitioners”, Journal of Microbiology & Experimentation, 2014, vol. 01, No. 05, pp. 179-184.

* cited by examiner

PARYLENE COATINGS FOR MEDICAL ARTICLES THAT ARE CLEANABLE AND REDUCE MICROBIAL TOUCH TRANSFER

SUMMARY

Disclosed herein are medical articles that have a barrier polymer coating that provides a cleanable surface and reduced microbial touch transfer. In some embodiments the articles are essentially flat with a polymeric layer and barrier polymer coating. In other embodiments, the articles are tubular. Also disclosed are methods for preparing medical articles.

In some embodiments, the medical article comprises a tube with an interior surface and an exterior surface, the tube comprising a polymer composition containing one or more extractable components, and a transparent vapor-deposited coating of a barrier polymer covering at least a portion of at least the exterior surface of the tube. The transparent vapor-deposited coating is derived from at least one ethylenically unsaturated monomer. The vapor-deposited polymer coating barrier reduces the extraction of extractable component(s) from the tube. The coating also provides a reduction in microorganism touch transfer of at least 20% and provides increased wet out of a cleaning solvent compared to an identical tube without the transparent vapor-deposited coating.

Also disclosed are methods of preparing medical articles. In some embodiments, the method comprises providing a tube with an interior surface and an exterior surface, where the tube comprises a polymer composition containing one or more extractable components, and vapor coating a barrier polymer derived from at least one ethylenically unsaturated monomer onto at least a portion of at least the exterior surface of the tube.

BRIEF DESCRIPTION OF THE DRAWINGS

The present application may be more completely understood in consideration of the following detailed description of various embodiments of the disclosure in connection with the accompanying drawings.

Figure 1:
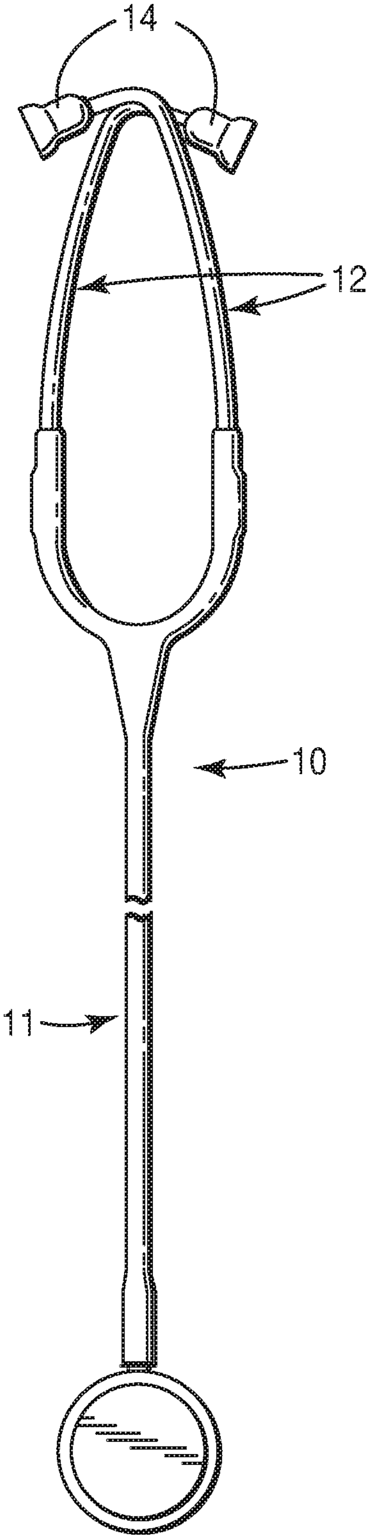
FIG. 1 is a top view of a stethoscope incorporating a tubing article of this disclosure.

In the following description of the illustrated embodiments, reference is made to the accompanying drawings, in which is shown by way of illustration, various embodiments in which the disclosure may be practiced. It is to be understood that the embodiments may be utilized and structural changes may be made without departing from the scope of the present disclosure. The figures are not necessarily to scale. Like numbers used in the figures refer to like components. However, it will be understood that the use of a number to refer to a component in a given figure is not intended to limit the component in another figure labeled with the same number.

DETAILED DESCRIPTION

Medical articles, since they are used in medical environments, are exposed to a wide range of environments, such as microbe-rich environments. This exposure can permit the medical articles to form a conduit for the spreading of microbes. A wide range of anti-microbial materials have been developed to treat surfaces to mitigate the transfer of microbes. There are a number of issues with the treatment of medical article surfaces with anti-microbial materials. In some instances, the use of anti-microbial materials on the surface of a medical article changes the properties of that medical article. For example, many anti-microbial materials give the surface of the medical article a greasy or oily feel which can be undesirable. In other instances, the anti-microbial material can change the appearance of the surface of the article, or can change the physical properties of the medical article. Particularly challenging in this regard are articles that are flexible, as described below.

Recently it has been found that articles with specific microstructure features are useful for reducing the initial touch transfer of microorganisms. Despite the anticipation that such microstructured surfaces can be difficult to clean, surprisingly, it has been found that some types of microstructured surfaces exhibit better microorganism (e.g. bacteria) removal when cleaned, even in comparison to smooth surfaces. This development is described in PCT Publication Nos. WO 2021/033162 and WO 2021/032368. These microstructured surfaces have a deliberately designed microstructure imparted to the surface, and it is not natural surface roughness. However, not all surfaces are suitable for having microstructural features imparted to them, and also there are medical articles where a microstructured surface is not suitable.

A wide range of medical devices and articles are prepared from polymeric materials. Many of these articles and devices desirably have flexibility. Beside the anti-microbial issues described above, flexible materials have additional complicating issues. Among the flexible materials used are polymers that contain extractable materials such as plasticizers, fillers, tackifiers, heat stabilizers, and the like. These extractable materials are often present in large quantities. The extractable materials can be extracted from the polymer by exposure to solvents, by heat, by contact with fluids such as aqueous or hydroalcoholic disinfectants, by high humidity (e.g. >90% relative humidity), by contact with skin, or even over time. This extraction is undesirable for many reasons and can cause difficulties in the use of the medical articles.

One particularly useful polymeric material is polyvinyl chloride (PVC) often referred to as “vinyl”. PVC by itself is a rigid material, and thus plasticizers are added to the material to make it softer and more flexible. Among the commonly used plasticizers are phthalates. In recent years, the use of phthalate plasticizers in PVC for medical uses has fallen into disfavor, and phthalate-free PVC materials are being used more and more in medical applications. However, as is well known in the chemical arts, making a change in composition often causes changes in the properties of the materials.

PVC materials are frequently used in tubing materials, such as the sound transmitting tubes of stethoscopes. These tubes have a variety of required property features. Among these properties are flexibility, resistance to degradation from exposure to heat and chemicals, durability, an aesthetically pleasant look, and a pleasant feel. The introduction of phthalate-free PVC materials has been observed to adversely affect some or all of these properties. As the stethoscopes are used, washing, and exposure to the body heat of the user tends to cause the PVC material to become more rigid as plasticizer leaches out or is washed away.

In addition to the requirements for flexibility, durability, and aesthetics, it is desirable to add the features of reduced microbial touch transfer and cleanability with disinfecting solutions. As was mentioned above, the addition of an anti-microbial agent to the surface of the flexible medical article can change the aesthetic or physical properties of the article. Therefore, there is a need for flexible articles that prevent the leaching of plasticizer from the flexible material, are cleanable with disinfecting solutions, and that reduce touch transfer without using an antimicrobial material or having a microstructured surface structure.

In this disclosure, it has been found that coating of polymeric medical articles that contain extractable components with a vapor-deposited coating of a polymer derived from at least one ethylenically unsaturated monomer not only reduces the extractability of the extractable components, but also provides a cleanable surface that reduces microbial touch transfer. In addition, the coating provides a variety of additional desirable features. Among these features are optical transparency and tactile features such as a desirable texture and coefficient of friction. Because the coating protects the article, the article retains its desirable properties over the lifetime of the article.

This disclosure includes medical articles that are flat articles as well as tubular articles. The methods of coatings disclosed herein are especially suitable for tubular articles, since tubular articles, especially flexible tubular articles, are difficult to coat.

Disclosed herein are flat articles comprising a polymer composition containing one or more extractable components, with a first major surface and a second major surface, wherein at least one of the first major surface and the second major surface comprises a vapor-deposited coating of a barrier polymer derived from at least one ethylenically unsaturated monomer.

Also disclosed herein are tubes useful in tubing articles, where the tubes comprise a polymer composition containing one or more extractable components, where the tube article has a vapor-deposited coating of a barrier polymer derived from at least one ethylenically unsaturated monomer on at least the exterior surface of the tube. In some embodiments, the vapor-deposited coating is present on both the interior and exterior surface of the tube. The barrier polymer is derived from at least one ethylenically unsaturated monomer and may be optionally crosslinked by incorporation of at least one dimeric ethylenically unsaturated monomer. The vapor-deposited barrier polymer coating reduces the extraction of extractable component(s) from the tube without blocking the anti-microbial activity of the anti-microbial agent present on the tube. Additionally, the protective coating provides a cleanable surface. By this it is meant that the surface is cleanable with disinfecting solutions, and also that if the surface becomes soiled or marked, the soiling or marking can be removed. In this way, the protective coating not only protects the article surface and permits the cleaning of the article surface, but also reduces the extraction of extractable components from the tube and provides a reduction of microbial touch transfer. Also disclosed are methods of preparing tubing articles, such as medical articles. Among the tubing articles are stethoscopes.

The term "tube" and "tubing" as used herein refers to a three-dimensional tubular article that is cylindrically symmetric. Tubes and tubing are defined by an inner diameter, an outer diameter, (the thickness of the tubing is the difference between the outer diameter and the inner diameter) and a length. While the thickness of the tubing can vary slightly through the length of the tube as the result of the method of preparation, etc., no intentional asymmetries are present in the tubing. Typically, the length is substantially greater than the diameter of the tube.

The term "microorganism" is generally used to refer to any prokaryotic or eukaryotic microscopic organism, including without limitation, one or more of bacteria (e.g., motile or nonmotile, vegetative or dormant, Gram positive or Gram negative, planktonic or living in a biofilm), bacterial spores or endospores, algae, fungi (e.g., yeast, filamentous fungi, fungal spores), mycoplasmas, and protozoa, as well as combinations thereof. In some cases, the microorganisms of particular interest are those that are pathogenic, and the term "pathogen" is used to refer to any pathogenic microorganism. Examples of pathogens can include, but are not limited to, both Gram positive and Gram negative bacteria, fungi, and viruses including members of the family Enterobacteriaceae, or members of the family Micrococaceae, or the genera *Staphylococcus* spp., *Streptococcus*, spp., *Pseudomonas* spp., *Acinetobacter* spp., *Enterococcus* spp., *Salmonella* spp., *Legionella* spp., *Shigella* spp., *Yersinia* spp., *Enterobacter* spp., *Escherichia* spp., *Bacillus* spp., *Listeria* spp., *Campylobacter* spp., *Acinetobacter* spp., *Vibrio* spp., *Clostridium* spp., *Klebsiella* spp., *Proteus* spp. *Aspergillus* spp., *Candida* spp., and *Corynebacterium* spp. Particular examples of pathogens can include, but are not limited to, *Escherichia coli* including enterohemorrhagic *E. coli* e.g., serotype O157:H7, O129:H11*; Pseudomonas aeruginosa; Bacillus cereus; Bacillus anthracis; Salmonella enteritidis; Salmonella enterica* serotype *Typhimurium; Listeria monocytogenes; Clostridium botulinum; Clostridium perfringens; Staphylococcus aureus*; methicillin-resistant *Staphylococcus aureus*; carbapenem-resistant Enterobacteriaceae, *Campylobacter jejuni; Yersinia enterocolitica; Vibrio vulnificus; Clostridium difficile*; vancomycin-resistant *Enterococcus; Klebsiella pnuemoniae; Proteus mirabilus* and *Enterobacter* [*Cronobacter*] *sakazakii.*

The term "(meth)acrylate" refers to monomeric acrylic or methacrylic esters of alcohols. Acrylate and methacrylate monomers or oligomers are referred to collectively herein as "(meth)acrylates". Materials referred to as "(meth)acrylate functional" are materials that contain one or more (meth) acrylate groups.

The terms "polysiloxane" and "siloxane-based" as used herein refer to polymers or units of polymers that contain siloxane units. The terms silicone or siloxane are used interchangeably and refer to units with dialkyl or diaryl siloxane (—$SiR_2O$—) repeating units.

The terms "room temperature" and "ambient temperature" are used interchangeably to mean temperatures in the range of 20° C. to 25° C.

Unless otherwise indicated, the terms "optically transparent", and "visible light transmissive" are used interchangeably, and refer to a layer, article, or film that has a high light transmittance over at least a portion of the visible light spectrum (about 400 to about 700 nm). Typically, optically transparent articles have a visible light transmittance of at least 90% and a haze of less than 10%.

The terms "polymer" and "macromolecule" are used herein consistent with their common usage in chemistry. Polymers and macromolecules are composed of many repeated subunits. As used herein, the term "macromolecule" is used to describe a group attached to a monomer that has multiple repeating units. The term "polymer" is used to describe the resultant material formed from a polymerization reaction.

The term "anti-microbial" is used herein according to the commonly used meaning, that is an agent that kills or stops the growth of microorganisms.

The term "alkyl" refers to a monovalent group that is a radical of an alkane, which is a saturated hydrocarbon. The alkyl can be linear, branched, cyclic, or combinations thereof and typically has 1 to 20 carbon atoms. In some embodiments, the alkyl group contains 1 to 18, 1 to 12, 1 to 10, 1 to 8, 1 to 6, or 1 to 4 carbon atoms. Examples of alkyl groups include, but are not limited to, methyl, ethyl, n-propyl, isopropyl, n-butyl, isobutyl, tert-butyl, n-pentyl, n-hexyl, cyclohexyl, n-heptyl, n-octyl, and ethylhexyl.

The term "aryl" refers to a monovalent group that is aromatic and carbocyclic. The aryl can have one to five rings that are connected to or fused to the aromatic ring. The other ring structures can be aromatic, non-aromatic, or combinations thereof. Examples of aryl groups include, but are not limited to, phenyl, biphenyl, terphenyl, anthryl, naphthyl, acenaphthyl, anthraquinonyl, phenanthryl, anthracenyl, pyrenyl, perylenyl, and fluorenyl.

The terms "free radically polymerizable" and "ethylenically unsaturated" are used interchangeably and refer to a reactive group which contains a carbon-carbon double bond which is able to be polymerized via a free radical polymerization mechanism.

As used herein the term "PVC" is used as a shorthand definition of polyvinyl chloride. The term "phthalate-free PVC" as used herein refers to a PVC material that does not contain phthalate plasticizer.

As used herein the term "plasticizer" refers to a compound(s) which when added to a polymer results in increased flexibility.

As used herein the term "parylene" is a trade name for a variety of chemical vapor-deposited poly(p-xylylene) polymers. The term is used herein as a generic name for members of a unique polymer series. The basic member of the series, called Parylene N, is poly-para-xylylene, a completely linear, highly crystalline material.

Parylene C, the second commercially available member of the series, is produced from the same monomer modified by the substitution of a chlorine atom for one of the aromatic hydrogens. The structures are shown below.

Parylene D, the third member of the series, is produced from the same monomer modified by the substitution of the chlorine atom for two of the aromatic hydrogens. Parylene D is similar in properties to Parylene C with the added ability to withstand higher use temperatures.

The parylene also may have one or more hydrogen atoms replaced by fluorine. For example, Parylene AF-4 and parylene VT-4 (generic name, per-fluorinated aromatic ring) also known as PARYLENE HT from SCS.

Parylene X is a crosslinkable parylene. Poly(methyl-p-xylylene) or parylene M

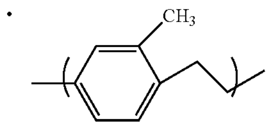

and Parylene E

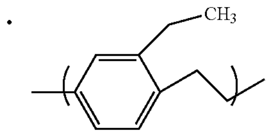

are solvent soluble polymers.

-continued

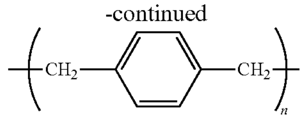

Parylene N

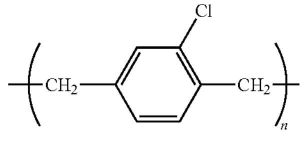

Parylene C

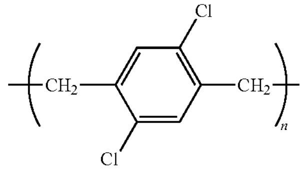

Parylene D

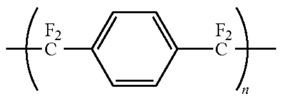

PARYLENE AF-4 or PARYLENE HT

As used herein "parylene copolymers" are chemical vapor-deposited derived from p-xylylene and at least one additional ethylenically unsaturated monomer.

As used herein "parylene coatings" refer to coatings of parylene materials.

Disclosed herein are medical articles prepared from polymeric materials with one or more extractable components. The articles may be tube-shaped or flat. In some embodiments, the articles are tubes useful to prepare tubing articles, especially medical articles. The tubes have an interior surface and an exterior surface and are prepared from a polymer composition containing one or more extractable components. The tubes have a vapor-deposited coating of a barrier polymer derived from at least one ethylenically unsaturated monomer covering at least the exterior surface of the tube. The vapor-deposited barrier polymer coating reduces the extraction of extractable component(s) from the tube, provides a surface cleanable with disinfectant solution, and reduces microbial touch transfer.

A wide range of polymer compositions containing one or more extractable components are suitable for preparing tubes. In some embodiments, the polymer compositions comprise plasticized polyvinyl chloride (PVC), plasticized PVC copolymers, plasticized polyurethane, or polysiloxanes. Polysiloxanes may or may not include plasticizers like the other classes of polymers, but even if plasticizers are not used in the polysiloxanes, they may contain a variety of extractable materials such as unreacted cyclic siloxane, catalyst residue, tackifier, or a combination thereof. Additionally, any of the above polymer compositions may contain additional materials that may be extractable including stabilizing agents such as thermal stabilizers and UV stabilizers, fillers, and the like.

Polyurethane polymers are well known in the polymer arts, being prepared from the reaction of poly-isocyanates and polyols. A wide range of polyurethane polymers are suitable, including aromatic, aliphatic, urethane block copolymers and copolymers and mixtures thereof. A wide range of plasticizers can be used to plasticize the polyurethane polymers. The polyurethanes may be linear or crosslinked.

The polyols used to prepare the polyurethanes may be poly-ether polyols, polyester polyols, aliphatic polyols, siloxane polyols, and the like. The crosslinked polyurethanes are generally made via a 2-part reaction.

Polysiloxane polymers are also well known in the art. Typically, siloxane-based polymers can be prepared in a variety of ways including moisture-curing, hydrosilylation, and condensation reactions. Additionally, a wide range of polysiloxane polymers and polysiloxane precursors are commercially available. As mentioned above, the polysiloxanes can contain a variety of extractable components. Additionally, it can be desirable to apply a barrier coating to polysiloxane tubes, not only as a barrier against leaching of extractable components but also to alter the surface properties of the polysiloxane tube. Polysiloxanes often have a tacky or sticky feel that can be undesirable. Additionally, while efforts are typically expended to ensure that no residual siloxane monomer is present in the polymer that is formed into a tube, these tasks can be labor intensive or expensive and can be avoided through the use of a barrier layer that inhibits or prevents the leaching of extractable material from the polymeric tube.

In many embodiments, the polymer compositions comprise plasticized PVC polymers and plasticized PVC copolymers. PVC copolymers are prepared by copolymerizing one or more ethylenically unsaturated co-monomers with vinyl chloride. An example of a PVC copolymer is polyvinyl chloride-vinyl acetate. Like the PVC polymers described below, the PVC copolymers typically contain plasticizers, often relatively high loadings of plasticizer.

One particularly suitable class of polymers for tubing articles, especially medical tubing articles are PVC polymers. PVC polymers tend to be rigid materials, and therefore plasticizers are added to make the polymers flexible. Typically, the PVC polymer compositions contain a large quantity of plasticizer. The PVC polymer compositions typically contain up to 50-60% by weight plasticizer based on the total weight of the tube composition. In some embodiments, the PVC polymer composition comprises at least 20% by weight plasticizer, typically at least 30% by weight plasticizer, more typically at least 35% by weight plasticizer, or even at least 40% or 45% by weight plasticizer by weight. Generally, the PVC polymer compositions comprise less than 60% by weight plasticizer or less than 55% by weight plasticizer.

As was mentioned above, the use of phthalate-free plasticizers is becoming more prevalent in the preparation of medical articles such as tubing articles. In some embodiments, the polymer composition of the tubes of this disclosure comprise PVC polymer compositions that are free of phthalate plasticizers.

Among the suitable classes of plasticizers are oligomeric or polymeric plasticizers having an average molecular weight of greater than 1000 Daltons, greater than 1500 Daltons, or even greater than 2000 Daltons as determined by GPC with the appropriate standards. Particularly suitable oligomeric or polymeric plasticizers are aliphatic or aromatic polyesters and are available from Hallstar under the PLASTHALL tradename or from Lanxess under the ULTRAMOL brandname.

Another suitable class of plasticizers are sulfonate esters such as MESAMOLL which is an alkylsulphonic acid ester with phenol.

Additional plasticizers include trimellitates such as trimethyl trimellitate, tri-(2-ethylhexyl) trimellitate, tri-(heptyl, nonyl) trimellitate and the like.

Aliphatic dicarboxylic acid-based plasticizers such as bis(2-ethylhexyl)adipate dimethyl adipate, dioctyl adipate, dibutyl sebacate, dibutyl maleate and the like.

Other plasticizers include azelates, benzoates, terephthalates such as dioctyl terephthalate/DEHT (Eastman Chemical Company Trademark: EASTMAN 168), 1,2-Cyclohexane dicarboxylic acid diisononyl ester (BASF trademark: HEXAMOLL DINCH).

Sulfonamides such as N-ethyl toluene sulfonamide (o/p ETSA), ortho and para isomers, glycols and polyethers such as triethylene glycol dihexanoate and tetraethylene glycol diheptanoate.

The polymeric tubes of this disclosure may have a wide range of diameters and thicknesses. Typically, the tubes are not wide tubes, often having an inner diameter of from 1 to 10 millimeters. In some embodiments, the tube has a thickness of from 0.1-7 millimeters. Generally, the tubes are at least 20 centimeters in length, more typically at least 40 centimeters in length.

The surface of the tubing article can have additional coatings or surface treatments. In some embodiments, the tubing articles further comprise a discontinuous or continuous layer on the exterior surface of the tube, where the discontinuous or continuous layer comprises a graphic layer such as a printed layer. The printed surface may be a continuous layer so that the printing covers the entire surface, or the printing may be in the form of a pattern. Typically, the printed surface comprises a printed pattern. A wide range of printed patterns can be used including printed designs, indicia, geometric patterns, and the like. Examples of suitable graphic layers that can be printed onto the article surface include such things as the patterns of UPC or QR codes, decorative patterns such as art and logos, and the like.

A wide range of printing techniques can be used to form the printed surface. In some embodiments, the printing can be carried out using conventional printing techniques such as screen printing and inkjet printing as well as a variety of contact printing techniques such as flexographic printing, patterned roll coating, letterpress printing, lithography, stencil printing, and the like. Because the tubes are three-dimensional articles, printing using the above conventional printing techniques can be difficult. One particularly suitable technique is hydrographic printing.

Hydrographic printing, also known as water transfer printing and immersion printing, is a method of applying printed designs to three-dimensional surfaces. In the process, a polyvinyl alcohol hydrographic film, which has been gravure-printed with the graphic image to be transferred, is carefully placed on the water's surface in a dipping tank. The clear film is water-soluble, and dissolves after applying an activator solution. Once dipping is begun, the surface tension of the water will allow the pattern to curve around any shape. Any remaining residue is then rinsed off thoroughly. The ink adheres to the desired surface and it cannot be washed off easily. It is then allowed to dry.

In other embodiments, the article is a flat article with a substrate layer with a first major surface and a second major surface. The flat articles are prepared from the polymeric compositions described above and include one or more extractable materials. The articles may be single layer articles or they may be multi-layer articles. The multi-layer articles may comprise layers of different polymeric materials. Like the tubular articles, the flat articles typically have a thickness of from 0.1-7 millimeters To the surface of the article, at least one ethylenically unsaturated monomer is vapor-deposited to form a polymer layer. The vapor-deposited polymer layer is an optically transparent barrier layer. Typically, the polymer barrier layer comprises parylene or a copolymer of parylene. Parylene is the trade name for vapor-deposited poly-para-xylylene. Poly para-xylylene, also referred to as parylene N, is shown in Formula 1 below:

Formula 1

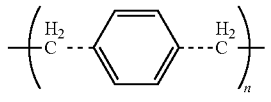

Parylene is prepared when the precursor [2,2]paracyclophane (shown in Formula 2 below) is heated above 550° C. in vacuum. Upon condensation on a surface, the poly-para-xylylene forms.

Formula 2

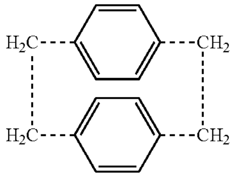

In some embodiments, the vapor-deposited coating of a crosslinked vinyl polymer comprises parylene, that is to say parylene N. In other embodiments, the vapor-deposited coating of a crosslinked vinyl polymer comprises a substituted parylene such as parylene C. Parylene C has the general structure shown in Formula 3 below. Parylene C is prepared by using a chlorine-substituted dimer.

Formula 3

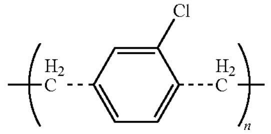

In some embodiments, the vapor-deposited coating of a barrier polymer comprises a copolymer of parylene and at least one (meth)acrylate. A wide variety of (meth)acrylates are suitable. In some embodiments, the (meth)acrylate comprises at least one $C_3$-$C_{18}$ alkyl (meth)acrylate.

The vapor-deposited coating of a barrier polymer can have a wide range of thicknesses. As mentioned above, the coating may be a continuous coating, present on the entire exterior surface of the tubing or it can be present in selective regions of the exterior surface of the tubing. Additionally, the coating may be present on both the interior and exterior surfaces of the tubing. In some embodiments, the vapor-deposited barrier polymer coating has a thickness of from 0.2-10 micrometers. In other embodiments, the vapor-deposited crosslinked vinyl polymer coating has a thickness of from 1-5 micrometers. The coating may have a uniform or essentially uniform thickness, or the coating thickness may vary over the surface of the tubing. Typically, the coating has an essentially uniform thickness.

The vapor-deposited coating of a barrier polymer may comprise additional additives. Among the additives are heat stabilizers, coloring agents, and mold release agents.

One necessary feature of the barrier polymers is their ability to strongly adhere to the tube. This is complicated by the fact that typically the tubing polymeric compositions contain high levels of plasticizer. Among the circumstances that make strong adhesion necessary is in bending. It is desirable that the barrier polymers are able to withstand 180° bending of the tubing for at least 5,000 cycles, more desirably at least 10,000 cycles and even more desirably at least 20,000 cycles when tested according to a "Bend Test" as is understood in the art.

The vapor-deposited coatings of a barrier polymer of the current disclosure reduce the extractability of the extractable components of the polymer compositions of the tubing and also provide for reduced touch transfer and/or increased microorganism (e.g. bacteria) removal when cleaned. Each of these features is described below.

In some embodiments, the coatings prevent the extraction of extractable components from the polymer compositions of the tubing. This extraction refers to a variety of extraction methods. It is particularly desirable that the barrier polymers prevent extraction by both polar fluids such as aqueous and hydroalcoholic (e.g. rubbing alcohol, 70/30 v/v isopropanol water) disinfectants as well as nonpolar fluids such as skin oil (sebum) and synthetic sebum. Examples of extraction methods include solvent extraction, heat extraction, and skin contact extraction. Solvent extraction involves the application of solvent to the polymer composition surface. Suitable solvents are described above and include polar fluids and nonpolar fluids. Upon removal of the solvent by wiping or similar techniques results in extractable components leaving the polymer composition. Heat extraction involves applying heat to the polymer composition which results in the extractable components leaching from the polymer composition. Heat can be used alone or in combination with the solvent extraction method described above. Skin contact extraction results from the contact of skin to the polymer composition where the extractable components in the polymer composition leach from the polymer composition. In practice, medical devices containing tubing articles can encounter each of these extraction methods, or a combination of them. The tubing article may be washed or cleaned with a solvent or other liquid, or the tubing may come into contact with a variety of fluids. Heat extraction can occur from contact with, for example, body heat, or higher temperatures such as, for example 50° C. if the article is left in a vehicle on a hot day. Similarly, skin contact extraction can occur from exposure of the tubing article to skin.

The extractability of extractable components from a polymer composition can be modeled in a variety of ways as is well understood in the art.

Touch transfer relates to surfaces exposed to the surrounding (e.g. indoor or outdoor) environment and is subject to being touched or otherwise coming in contact with multiple people and/or animals, as well as other contaminants (e.g. dirt). The test method used for studying the reduction of touch transfer is described in the Examples section below, but can be summarized as the comparison of the surface of interest, in this case a parylene-coated surface, to the surface without the parylene coating. Typically, the reduction of touch transfer is at least 20%. In some embodiments, the reduction of touch transfer is 25, 30, 35, 40, 45, 50, 60, 70, 80, 90, or 95%.

Closely related to the reduction of touch transfer is the increased cleanability of the parylene-coated surface relative to a surface without the parylene coating. The increased cleanability is evidenced by increased wet out of cleaning solvents. In some embodiments, the coated surface can prevent an aqueous or (e.g. isopropanol) alcohol based cleaning solution from beading up as compared to an uncoated surface. When a cleaning solution beads up or in other words dewets, the disinfectant agent may not be in contact with a microorganism for a sufficient duration of time to kill the microorganism. However, it has been found that at least 50, 60, 70, 80, or 90% of the microstructured surface can comprise cleaning solution 1, 2, and 3 minutes after applying the cleaning solution to the coated surface (according to the test method described in the examples).

In some embodiments, the cleaning solution is isopropanol or an isopropanol-based solution. The cleaning solution may contain an antiseptic component. Various antiseptic components are known including for example biguanides and bisbiguanides such as chlorhexidine and its various salts including but not limited to the digluconate, diacetate, dimethosulfate, and dilactate salts, as well as combinations thereof, polymeric quaternary ammonium compounds such as polyhexamethylenebiguanide; silver and various silver complexes; small molecule quaternary ammonium compounds such as benzalkoium chloride and alkyl substituted derivatives; di-long chain alkyl (C8-C18) quaternary ammonium compounds; cetylpyridinium halides and their derivatives; benzethonium chloride and its alkyl substituted derivatives; octenidine and compatible combinations thereof. In other embodiments, the antimicrobial component may be a cationic antimicrobial or oxidizing agent such as hydrogen peroxide, peracetic acid, bleach.

Besides the reduction of extractability of the extractable components of the polymer composition of the tubing and the reduction of touch transfer and/or improved cleanability, in some embodiments, the vapor-deposited coating changes the texture, the coefficient of friction, or a combination thereof. This can be particularly true of polysiloxane tubes which, as described above, can have a tacky or sticky feel.

The coated tubing of the current disclosure can be used to prepare a wide variety of medical articles. One particularly suitable use is for the tubing of stethoscopes. A typical stethoscope is shown in FIG. 1. FIG. 1 shows a top view of stethoscope 10. Stethoscope 10 has tubing 11 attached to dual sound transmitting tubes 12, terminating in ear tips 14. The elements of stethoscope 10 can vary from those shown, but the fundamental elements are present. This disclosure relates to tubing 11. The reduction of the extractability of plasticizer is one of the features desired for the tubing 11. Among these features are flexibility, handleability, and pleasing aesthetics. In many cases tubing 11 is prepared from plasticizer-filled PVC polymer. Flexibility is imparted to the PVC polymer by high levels of plasticizer, and retention of this plasticizer within the polymer matrix, in other words the lack of plasticizer extraction, is important to the usefulness of the tubing. Because the PVC polymer, or other polymeric material if used, often have high levels of plasticizer or other extractable components, migration of the plasticizer out of the polymer can occur over time, or the plasticizer can be extracted by washing or cleaning, or by contact with skin either when worn or when handled. Loss of flexibility of the tubing reduces the usefulness of the stethoscope. Handleability relates to the feel of the tubing, which is going to be worn and handled by the user of the stethoscope. Another important feature of handleability also relates to the lack of plasticizer extraction in that if plasticizer exudes from the tubing, the feel of the tubing becomes unpleasant and plasticizer can be transferred to the user's hand. A variety of aesthetic features including printed patterns, color, texture, gloss, and feel are desirable for the tubing of the stethoscope. Because the tubing comes into frequent contact with skin, the texture and feel of the tubing should be aesthetically pleasant, meaning that the tubing should be smooth and have a low coefficient of friction.

Figure 2:
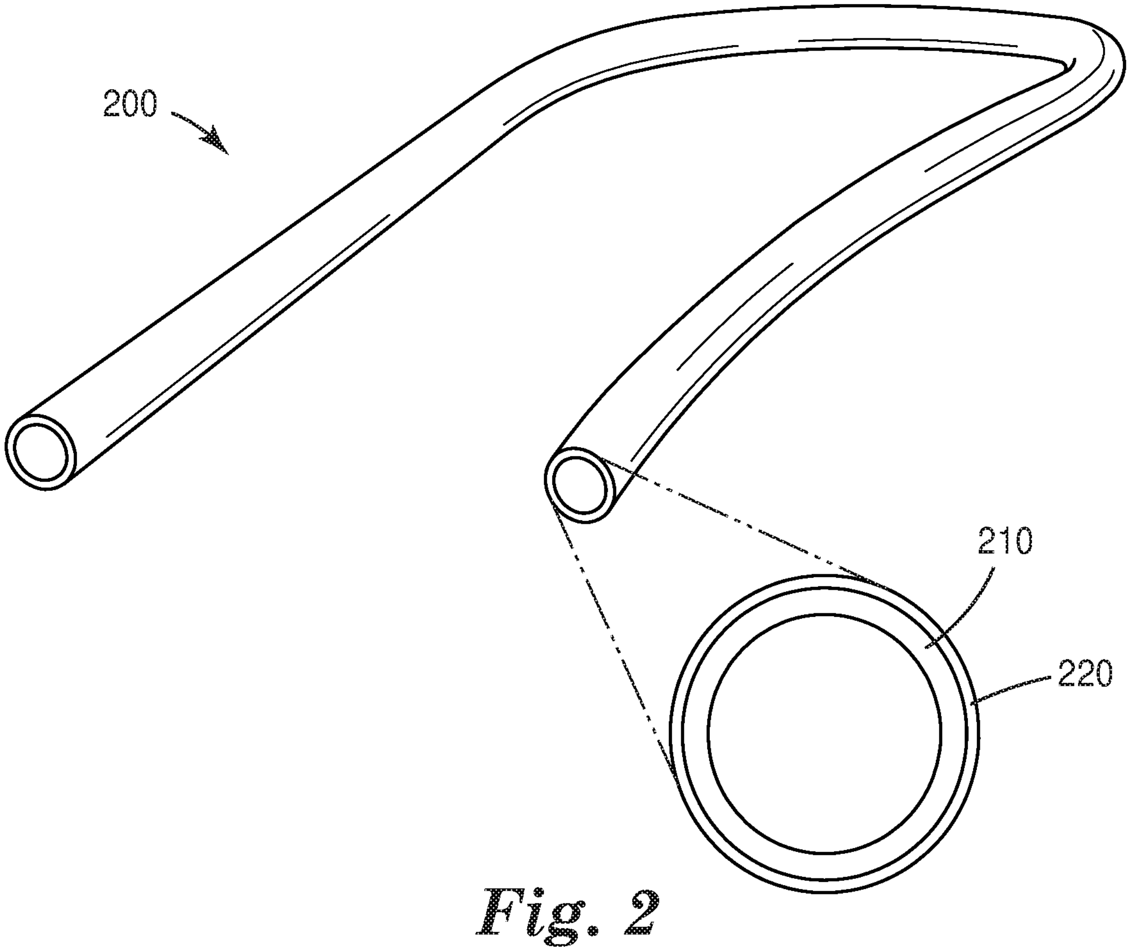
FIG. 2 is a top view of coated tubing of this disclosure, including a cross sectional view of a segment of the coated tubing.

FIG. 2 shows a cross-sectional view of a tubing article of this disclosure. Tubing article 200 has tubing layer 210 with transparent coating layer 220. Transparent coating layer 220 is a vapor-coated barrier layer.

Figure 3:
FIG. 3 is cross-sectional view of a flat article of this disclosure.

FIG. 3 shows a cross-sectional view of a flat article of this disclosure. Flat article 300 has substrate layer 310 with transparent coating layer 320. Transparent coating layer 320 is a vapor-coated barrier layer.

The performance of the coating layer, that is to say the prevention of the extraction of plasticizers from the polymeric material of the tubing article while at the same time providing a surface that has reduced touch transfer of microbial agents and/or increased cleanability is unexpected. As mentioned above, it has been found that microstructured surfaces display the features of reduced touch transfer and increased cleanability as described in PCT Publication Nos. WO 2021/033162 and WO 2021/032368. A close observation of the vapor-coated surface (for example by Scanning Electron Microscopy or SEM) shows that the vapor-coated surfaces are not perfectly smooth but rather include microcracks. While not wishing to be bound by theory, it is believed that these microcracks in the vapor-deposited coating may be functioning in a way similar to a microstructured surface.

Figure 4:
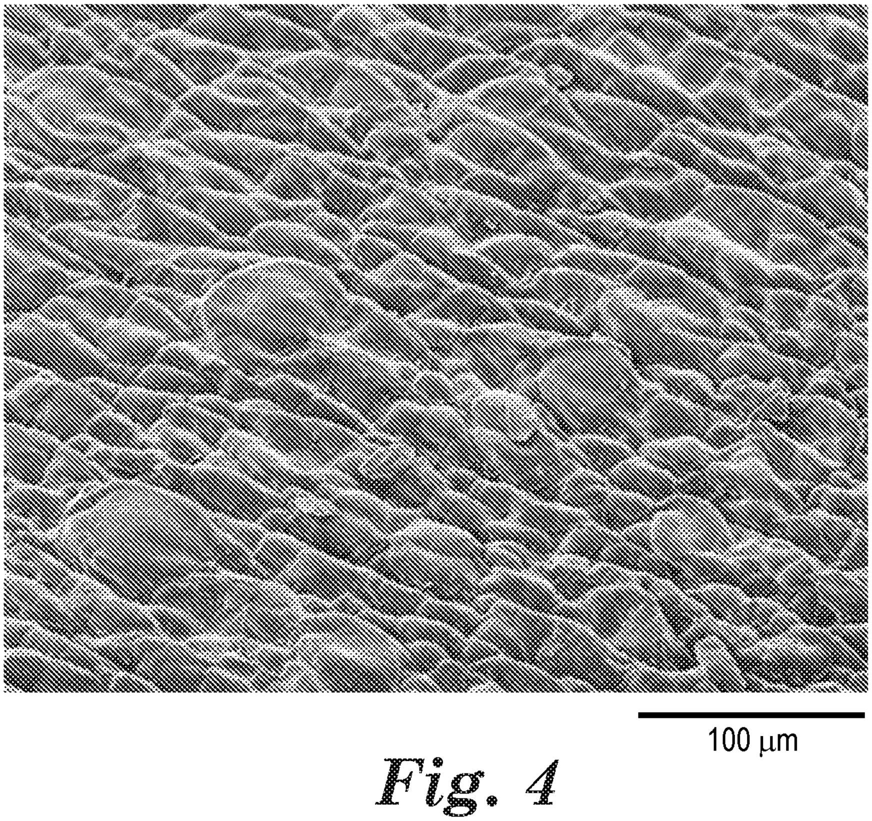
FIG. 4 is a SEM (Scanning Electron Micrograph) of the surface of a coated article of this disclosure.

The microcracks in the coating surface are visible in FIG. 4. Again, not wishing to be bound by theory, it is believed that the microcracks are at least partially responsible for the flexibility of the vapor-deposited coating. Because the polymeric materials are flexible and undergo bending, the microcracks are believed to provide a mechanism for the vapor-deposited coating to also bend and flex and not shatter when the tubing is bent or twisted. In this way, the coating remains largely intact and is also flexible. This is especially true for tubular articles.

Also disclosed are methods for preparing medical articles. In embodiments of medical articles that are flat, the method comprises providing a substrate layer with a first major surface and a second major surface, and vapor coating a barrier polymer derived from at least one ethylenically unsaturated monomer onto at least a portion of the exterior surface of the tube. Suitable substrate layers are described above.

In some embodiments, the method comprises providing a tube with an interior surface and an exterior surface, and vapor coating a barrier polymer derived from at least one ethylenically unsaturated monomer onto at least a portion of the exterior surface of the tube. The barrier polymer may be coated on the entire exterior surface of the tube and may also be coated on the interior surface of the tube, as has been described above. The polymeric tubing has been described above and comprises a polymer composition containing one or more extractable components.

In some embodiments, vapor coating a barrier polymer onto at least a portion of the exterior surface of the tube comprises placing the tube in a deposition chamber, applying a vacuum to the deposition chamber, heating a precursor material to volatize and optionally pyrrolyze at least a portion of it, and introducing the volatilized and optionally pyrrolyzed precursor material into the deposition chamber. The precursor material comprises the at least one ethylenically unsaturated monomer. Typically, the precursor material comprises parylene or a mixture of parylene and at least one (meth)acrylate. Suitable parylene compositions are described above. As was described above, the volatilized precursor material deposits on the tubing and polymerizes to form the barrier coating on the tubing surface. At least a portion of the exterior surface of the tubing is coated, and in many embodiments, the entire exterior surface of the tubing is coated. In some embodiments, both the interior and exterior surface of the tubing is coated. Typically, the vapor-deposited coating is optically transparent.

There are a variety of methods for placing the tubing in the deposition chamber. In some embodiments, the tubing may be placed on a rotating basket or it may be hung from a rack in the deposition chamber.

The tubing suitable for use in the methods of this disclosure are polymeric compositions with extractable components. Examples of suitable polymeric compositions have been described above. In some embodiments, the polymer compositions comprise plasticized polyvinyl chloride (PVC), plasticized PVC copolymers, plasticized polyurethane, or polysiloxanes. Polysiloxanes may or may not include plasticizers like the other classes of polymers, but even if plasticizers are not used in the polysiloxanes, they may contain a variety of extractable materials such as unreacted cyclic siloxane, catalyst residue, tackifier, plasticizer, or a combination thereof. Additionally, any of the above polymer compositions may contain additional materials that may be extractable including stabilizing agents such as thermal stabilizers and UV stabilizers, fillers, and the like.

The polymeric tubes of this disclosure may have a wide range of diameters and thicknesses. Typically, the tubes are not wide tubes, often having an internal diameter of from 1 to 10 millimeters. In some embodiments, the tube has a thickness of from 0.1-7 millimeters. The tube may have a variety of lengths, typically at least 20 centimeters, often at least 40 centimeters.

The vapor-deposited crosslinked polymer coatings have been described above. Typically, the polymer coating has a thickness of from 0.2-10 micrometers. In some embodiments, the polymer coating has a thickness of from 1-5 micrometers.

As mentioned above, the coated tubing can be used to prepare a wide variety of medical articles. In some embodiments, the coated tubes are used in stethoscopes, as has been described above.

The tubes of this disclosure also have a vapor-deposited coating of a barrier polymer derived from at least one ethylenically unsaturated monomer covering at least a portion of the exterior surface of the tube. For example, stethoscope tubing is desirably coated at least along the part of the tubing which would contact the skin when worn around the neck. In many embodiments, the entire exterior surface of the tube has a vapor-deposited coating of a barrier polymer. In some embodiments, the tube also has a vapor-deposited coating of a barrier polymer on the interior surface of the tube.

EXAMPLES

These examples are merely for illustrative purposes only and are not meant to be limiting on the scope of the appended claims. All parts, percentages, ratios, etc. in the examples and the rest of the specification are by weight, unless noted otherwise. The following abbreviations are used: mm=millimeters; nm=nanometers; g=grams; mL=milliliter; L=liter; rpm=revolutions per minute; h=hours.

Table of Abbreviations

| Abbreviation or Trade Designation | Description |
|---|---|
| PVC | Polyvinyl chloride tubes or pucks containing PolyOne phthalate-free plasticizer |
| RODAC Plate | Replicate Organism Detection And Counting, Fisher, Cat. No. 221238 |

Sample Preparation

Examples E1-E4 and Comparative Examples CE1 and CE2

Comparative Examples CE1: Uncoated Flat PVC

Samples of flat pucks of PVC were used to compare with the Parylene coated samples described below.

Examples E1-E3 PVC Flat Samples Coated with Parylene-C or Parylene-N

Samples of flat pucks of PVC were coated using a vacuum process statically hanging them from a rotating carousel. The samples were wiped once with isopropanol and loaded onto the carousel and placed into a parylene-coating reactor. The pucks were coated using a vacuum process at approximately 160 milliTorr. Coatings were: 2.1 micrometer thickness of Parylene-C (E1); 4.56 micrometer thickness of Parylene-N (E2); and 0.81 micrometer thickness of Parylene-C (E3).

Prior to parylene coating, the PVC pucks had a glossy finish and slightly tacky feel with a relatively high coefficient of friction. After application of the Parylene-C or Parylne N coating, the Parylene-coated pucks had a dry, slippery feel and a lower coefficient of friction. Parylene-N films give the sample a very uniformly matte finish. Parylene-C films remained glossy in appearance but with a fine elephant skin finish. sample flexibility was not changed with either coating. The strong adhesion of the Parylene coatings were confirmed by cutting a cross hatch pattern in the coating, adhering and removing a tape sample (3M Double Sided Tape) to determine if the coating was removed, similar to the "ASTM D3359 Cross Hatch Test" test method. The Parylene coatings were not removed upon removal of the tape.

Comparative Examples CE2: Uncoated Tubular PVC

Samples of tubes of PVC were used to compare with the Parylene coated sample described below.

Example E4 PVC Tubular Sample Coated with Parylene-C

Samples of tubes of PVC were coated using a vacuum process statically hanging them from a rotating carousel. The samples were wiped once with isopropanol and loaded onto the carousel and placed into a parylene-coating reactor. The tubes were coated using a vacuum process at approximately 160 milliTorr. Coatings of 2.1 micrometer thickness of Parylene-C. The coating process coated both interior and exterior surfaces of the tubing.

Prior to parylene coating, the PVC tubes had a glossy finish and slightly tacky feel with a relatively high coefficient of friction. After application of the Parylene-C coating, the Parylene-coated tubes had a dry, slippery feel and a lower coefficient of friction. Tubing flexibility was not changed with coating. The strong adhesion of the Parylene coating was confirmed by cutting a cross hatch pattern in the coating, adhering and removing a tape sample (3M Double Sided Tape) to determine if the coating was removed, similar to the "ASTM D3359 Cross Hatch Test" test method. The Parylene coatings were not removed upon removal of the tape.

Scanning electron micrograph (SEM) of a Parylene coated sample for Example E4 (Parylene-C) is shown in FIG. 3. FIG. 3 shows the microcracking present in the Parylene coating.

Sample Testing

Surface Roughness

Surface roughness of coated and uncoated flat and tubular samples was measured using a profilometer. The results are shown in Table 1 below, where Ra is the arithmetic average of the absolute values of the profile height deviations from the mean line, and Rq is the RMS (root mean square) value.

TABLE 1

| Sample | Ra (micrometers) | Rq (micrometers) |
|---|---|---|
| CE1 | 0.1156 | 0.2118 |
| CE2 | 0.2652 | 0.5198 |
| E1 | 1.0094 | 1.3134 |
| E2 | 1.6812 | 2.2274 |
| E4 | 0.9928 | 1.2970 |

The PVC uncoated tubes and pucks were relatively smooth. The roughness of Parylene C and N coated samples have ~10-15× higher Ra and Rq values compared to PVC with no coating. Parylene C coatings do not appear to be as rough as Parylene N coatings.

Disinfectant Wicking Evaluation:

Samples of CE2 and E4 were wiped using WypALL L30 General Purpose Wipers (nylon reinforced paper towels) soaked in a isopropyl alcohol containing 0.025% Crystal Violet (1 mL of 1% Crystal Violet per 40 mL) and excess liquid was squeezed out. Photographs were taken 1 minute after wiping. The dye was then wipe off using 100% isopropyl alcohol to clean off the crystal violet dye and another photograph was taken. Comparison of the images serve as a qualitative assessment for how isopropyl alcohol spread and de-wets from tubing then subsequently how the dye stained the tubing material. The crystal violet dye removed easily from the Parylene coated tube but stained the uncoated PVC tube permanently.

Touch Transfer Reduction Testing

Sample Preparation

Bacterial Inoculum Preparation: Tryptic Soy Agar was prepared per the manufacturer's instructions on the bottle. A streak plate of *Staphylococcus aureus* (ATCC 6538) was prepared from a frozen stock on Tryptic Soy Agar and left at 37° C. overnight to incubate. Two colonies from the plate were used to inoculate 9 mL of sterile Butterfield's Buffer (flip top tube). The optical density (absorbance) was read at 600 nm, to confirm that the reading was 0.040±0.010, it was adjusted as necessary to fall in this range, and then 1.5 mL of the culture was added to 45 mL of Butterfield's Buffer in a sterile 50-mL conical tube to make the inoculation solution for the touch transfer experiment. Each inoculation solution was enumerated using Butterfield's Buffer and serial dilutions were plated on 3M AEROBIC COUNT Petrifilm to confirm the cell concentration for each experiment.

Sample Preparation: Individual film samples were cut to 50±2×50±2 mm squares of control and microstructured test films and adhered to the bottom of a sterile 100-mm Petri dish using a small piece of 3M Double Sided Tape. Each sample was wiped three times using a KimWipe wet with 95% isopropyl alcohol. Samples were dried under the fan in a BioSafety Cabinet for 15 minutes then sterilized by irradiation of the apical surface using the BioSafety Cabinet's UV light for 30 minutes. For tube samples, a 50 mm long section was cut and used instead with no other modifications to the experiment.

Inoculation of Samples: Twenty-five mL of the inoculation solution was poured into a sterile 100-mm Petri dish. For each sample, an autoclave-sterilized 42.5 mm circle of Whatman Filter Paper (Grade 2) was immersed in the Petri dish containing the inoculation solution for 5 seconds using flame-sterilized tweezers. The carrier was removed and held over the Petri dish for 25 seconds for excess inoculum to drain. The inoculated paper was placed on top of the film sample and an autoclave-sterilized piece of Whatman Filter paper (Grade 2, originally 90-mm circle cut to a 60×60 mm square prior to autoclave sterilization) was placed on top of the inoculated sample. A sterile cell spreader was pressed on top of the sample and moved across the surface twice in perpendicular directions. The sample was left to sit for 2 minutes with both pieces of filter paper on top of the film. After the 2 minute exposure, both pieces of filter paper were removed with sterile tweezers and discarded in a biohazardous waste container and the sample was allowed to air dry at room temperature for 5 minutes. Touch transfer of the inoculated bacteria was assessed by pressing a RODAC plate evenly onto the sample (microstructured or smooth control) for 5 seconds using uniform pressure (~300 g). The RODAC plates were incubated at 37° C. overnight (18-24 h) and the number of colony forming units (CFU) were counted and recorded the following morning. Each microstructured sample and smooth control samples were performed in triplicate.

Results

Data Analysis: The $\log_{10}$ reduction in touch transfer was calculated by performing a $\log_{10}$ transformation on the number of CFU per RODAC plate, then calculating the $\log_{10}$ reduction by subtracting the $\log_{10}$ value from the microstructured sample from the $\log_{10}$ value from the corresponding smooth film control. The % reduction was then calculated on from the average $\log_{10}$ reduction from the following equation:

$$\%\,\text{Reduction} = \left(1 - 10^{(-\log_{10}\text{reduction value})}\right) * 100$$

The results are presented in Table 2 below. Both Parylene C and Parylene N coatings reduce touch transfer of microorganisms on flat pucks and tubes compared to uncoated PVC.

TABLE 2

| Sample | Average CFU | Log10 Average | Log 10 Reduction | % Reduction |
|---|---|---|---|---|
| CE1 | 256 | 2.36 | N/A | N/A |
| E1 | 106 | 2.02 | 0.34 | 55 |
| E2 | 99 | 1.99 | 0.37 | 58 |
| E3 | 196 | 2.28 | 0.08 | 17 |
| CE2 | 23 | 1.35 | N/A | N/A |
| E4 | 8 | 0.69 | 0.66 | 78 |

What is claimed is:

1. A medical article comprising:

a tube with an interior surface and an exterior surface, comprising a polymer composition containing one or more extractable components; and a transparent vapor-deposited coating of a barrier polymer derived from at least on ethylenically unsaturated monomer covering at least a portion of at least the exterior surface of the tube, such that the vapor-deposited coating reduces the extraction of extractable component(s) from the tube, provides a reduction in microorganism touch transfer of at least 20% and provides increased wet out of cleaning solvent compared to an identical tube without the vapor-deposited coating, wherein the vapor-deposited coating has at least one crack.

2. The medical article of claim 1, wherein the vapor-deposited coating covers at least a portion of the interior surface of the tube.

3. The medical article of claim 1, wherein the article has a reduction in microorganism touch transfer of at least 50%.

4. The medical article of claim 1, wherein the polymer composition containing one or more extractable components comprises:

plasticized polyvinyl chloride (PVC);

plasticized PVC copolymers;

plasticized polyurethane; or polysiloxane containing unreacted cyclic siloxane, catalyst residue, plasticizer, tackifier, or a combination thereof.

5. The medical article of claim 1, wherein the vapor-deposited barrier polymer comprises parylene.

6. The medical article of claim 5, wherein parylene comprises parylene N, parylene C, parylene D, or parylene HT.

7. The medical article of claim 1, wherein the vapor-deposited coating has a thickness of from 0.2-10 micrometers.

8. The medical article of claim 1, wherein the vapor-deposited coating has a thickness of from 1-5 micrometers.

9. The medical article of claim 1, wherein the polymer composition containing one or more extractable components has a thickness of from 0.1-7 millimeters.

10. The medical article of claim 1, wherein the tube comprises tubing for a stethoscope.

11. The medical article of claim 1, wherein the vapor-deposited coating comprises a copolymer of parylene and at least one (meth)acrylate.

12. A medical article comprising:

a first major surface and a second major surface, comprising a polymer composition containing one or more extractable components; and a transparent vapor-deposited coating of a barrier polymer derived from at least one ethylenically unsaturated monomer covering at least a portion of the first major surface, such that the vapor-deposited coating reduces the extraction of extractable component(s) from the tube, and provides a reduction in microorganism touch transfer of at least 20% and provides increased wet out of cleaning solvent compared to an identical article without the transparent vapor-deposited coating, wherein the vapor-deposited coating has at least one crack.

13. The medical article of claim 12, wherein the article has a reduction in microorganism touch transfer of at least 50%.

14. The medical article of claim 12, wherein the polymer composition containing one or more extractable components comprises:

plasticized polyvinyl chloride (PVC);

plasticized PVC copolymers;

plasticized polyurethane; or polysiloxane containing unreacted cyclic siloxane, catalyst residue, plasticizer, tackifier, or a combination thereof.

15. The medical article of claim 12, wherein the vapor-deposited barrier polymer comprises parylene N, parylene C, parylene D, or parylene HT.

16. The medical article of claim 12, wherein the vapor-deposited coating has a thickness of from 0.2-10 micrometers.

17. A method of preparing a medical article comprising:

providing a tube with an interior surface and an exterior surface, comprising a polymer composition containing one or more extractable components; and vapor coating a barrier polymer derived from at least one ethylenically unsaturated monomer onto at least a portion of at least the exterior surface of the tube to form a vapor-deposited coating that has at least one crack, wherein the vapor-deposited coating is transparent, and wherein the vapor-deposited coating reduces the extraction of extractable component(s) from the tube, provides a reduction in microorganism touch transfer of at least 20%, and provides increased wet out of cleaning solvent compared to an identical tube without the vapor-deposited coating.

18. The method of claim 17, wherein vapor coating a barrier polymer onto at least a portion of at least the exterior surface of the tube comprises:

placing the tube in a deposition chamber;

applying a vacuum to the deposition chamber;

heating a precursor material to volatize at least a portion of it; and introducing the volatilized precursor material into the deposition chamber, wherein the precursor material comprises parylene or a mixture of parylene and at least one (meth)acrylate.

19. The method of claim 17, wherein the vapor-deposited coating has a thickness of from 0.2-10 micrometers.

20. The method of claim 17, wherein the tube comprises tubing for a stethoscope.

* * * * *